US00PP24774P3

(12) United States Plant Patent

Skotak, Jr.

(10) Patent No.: US PP24,774 P3

(45) Date of Patent: Aug. 19, 2014

(54) *ANANAS* PLANT NAMED 'DURANAS2'

(50) Latin Name: *Ananas comosus*
Varietal Denomination: Duranas2

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 108 days.

(21) Appl. No.: 13/573,599

(22) Filed: Sep. 26, 2012

(65) Prior Publication Data

US 2014/0090119 P1 Mar. 27, 2014

(30) Foreign Application Priority Data

Sep. 24, 2012 (QZ) ..... PBR 20122017

(51) Int. Cl.
*A01H 5/00* (2006.01)

(52) U.S. Cl.
USPC ..... Plt./156

(58) Field of Classification Search
USPC ..... Plt./156
See application file for complete search history.

*Primary Examiner* — Annette Para

(74) *Attorney, Agent, or Firm* — Cassandra Bright

(57) ABSTRACT

A new and distinct *Ananas comosus* cultivar named 'Duranas2' is disclosed, characterized by a very compact plant shape, medium fruit size and suitability as an indoor pot plant.

1 Drawing Sheet

Latin name of the genus and species: *Ananas comosus.*
Variety denomination: 'Duranas2'.

BACKGROUND OF THE INVENTION

This application concerns a new cultivar of *Ananas*, described in EU application number 2012/2017, filed Sep. 24, 2012, to which inventor claims priority. The new cultivar is a product of a planned breeding program. The new variety originated from a cross pollination of an unnamed proprietary seedling of *Ananas comosus* with a different unnamed proprietary seedling of *Ananas comosus*. The new variety was selected by the inventor, Chester Skotak Jr., a citizen of Costa Rica, in Ajauela, Costa Rica during 2005, in a group of seedlings resulting from the crossing.

Asexual reproduction of the new cultivar 'Duranas2' was first performed in Costa Rica by tissue culture, during 2006, at a non-commercial laboratory in Costa Rica. 'Duranas2' has since been reproduced over several generations and has shown that the unique features of this cultivar are stable and reproduced true to type.

SUMMARY OF THE INVENTION

The cultivar 'Duranas2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Duranas2' These characteristics in combination distinguish 'Duranas2' as a new and distinct *Ananas comosus* cultivar:

1. Extremely compact, bushy plant shape.
2. Medium sized fruit.
3. Suitability as an indoor pot plant.

Plants of the new cultivar 'Duranas2' are similar to both parent varieties in some horticultural characteristics. However, 'Duranas2' differs from both the seed and pollen parents in having a smaller fruit and shorter leaves.

COMMERCIAL COMPARISON

'Duranas2' is best compared to the patented commercial variety *Ananas comosus* 'Duranas', U.S. Plant Pat. No. 22,402. Plants of 'Duranas' are similar to plants of 'Duranas2' in most horticultural characteristics, however, plants of 'Duranas2' are even more compact, and produce fruit that is larger than the fruit produced by plants of 'Duranas'.

BRIEF DESCRIPTION OF THE PHOTOGRAPH

The accompanying photograph in FIG. 1 illustrates in full color a typical plant of 'Duranas2' grown in a greenhouse. This plant is approximately 9 months old, shown in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Duranas2' plants grown in a climate controlled greenhouse in Alajuela, Costa Rica. Temperatures ranged from 20° C. to 24° C. night and day. No artificial light, photoperiodic treatments or chemical treatments were given to the plants. Measurements and numerical values represent averages of typical plant types.

Botanical classification: *Ananas comosus* cultivar 'Duranas2'.

PROPAGATION

First propagation method: Tissue culture.
Type of propagation typically used: Tissue Culture.

Time to initiate roots: About 90 days at approximately 24° C.
Time to produce a rooted cutting/liner: About 90 days at approximately 24° C.

PLANT

Age of the plant described: Approximately 9 months.
Pot size of the plant described: 12 cm commercial pot.
Growth habit: Basal rosette with inflorescence growing from the centre.
Height: Average height to top of leaf plane: 23.0 cm, average height to top of plant: 23.8 cm.
Plant spread: Average: 50.0 cm.
Normal pot size: 12 cm.
Growth rate: Low to moderate.
Branching characteristics: Basal rosette.
Number of leaves per stem: Average 45 per rosette.
Stem length: No stems present, basal rosette growing from the roots.

FOLIAGE

Leaf:
*Arrangement*.—Placed in a basal rosette.
*Average length*.—Approximately 24.6 cm.
*Average width*.—Approximately 2.1 cm.
*Shape of blade*.—Linear.
*Aspect*.—Curved downward, very slightly twisted.
*Apex*.—Long acuminate, sharply pointed.
*Base*.—Sheath length: Average 2.2 cm. Sheath width: Average 2.8 cm. Sheath color: Yellow-green; near RHS-CC 144B and 146D, both colors present covered with a greyed-white layer, very difficult to measure with RHS-CC but closest to near RHS-CC 156D.
*Margin*.—Entire.
*Texture of top surface*.—Smooth, glossy.
*Texture of bottom surface*.—Smooth, dull.
*Color*.—Young foliage upper side: Green; near RHS-CC N137B, base yellow-green; near RHS-CC 144B. Young foliage under side: Green; near RHS-CC 137A, base lighter; near RHS-CC 138B. Surface densely covered with a greyed-green waxy layer; 190B. Mature foliage upper side: Yellow-green; near RHS-CC 147A but darker. Mature foliage under side: Greyed-green; near RHS-CC 191A, densely covered with a greyed-green waxy layer; 190B.
*Venation*.—Type: parallel. Venation coloration: Indistinguishable from leaf surface.
Petiole: No petioles present.

INFLORESCENCE

*Inflorescence height, excluding scape*.—Approximately 11.0 cm.
*Inflorescence width*.—Approximately 14.0 cm.

Scape:
*Length*.—Approximately 14.1 cm.
*Width*.—Approximately 1.2 cm.
*Aspect*.—Approximately 90° angle to rosette (0°=horizontal).
*Strength*.—Very strong.
*Color*.—Yellow-green; near RHS-CC 146B, moderately covered with a greyed-green waxy layer; 190D.
Bracts:
*Scape/lowermost bracts*.—Shape: linear. Length: Approximately 7.3 cm, excluding sheath. Width: Approximately 0.9 cm. Quantity: Average 9. Tip: narrow acuminate, sharply pointed. Base: decurrent. Sheath length: Approximately 0.9 cm. Sheath width: Approximately 1.4 cm. Sheath color: Yellow-green; near RHS-CC 144B, covered with a greyed-white layer, very difficult to measure with RHS-CC but closest to near RHS-CC 156D. Margin: Entire. Color Upperside: Yellow-green; near RHS-CC 147A but darker. Color Underside: Greyed-green; near RHS-CC 191A, densely covered with a greyed-green waxy layer; 190B.
*Terminal bracts*.—Shape: linear-lanceolate. Length: Approximately 2.5 cm, excluding sheath. Width: Approximately 1.3 cm. Quantity: Average 42. Tip: acuminate, sharply pointed. Base: decurrent. Sheath length: Approximately 0.6 cm. Sheath width: Approximately 1.4 cm. Sheath color: Yellow-green; near RHS-CC 144C, slightly covered with a greyed-white layer, very difficult to measure with RHS-CC but closest to near RHS-CC 156D. Margin: Entire. Coloration Terminal Bracts: Upperside: Yellow-green; near RHS-CC 147A but darker. Underside: Greyed-green; near RHS-CC 191A, densely covered with a greyed-green waxy layer; 190B.

OTHER CHARACTERISTICS

Fruit/seed production:
*Shape*.—Ovate.
*Length* (*height*).—Average: 5.1 cm.
*Width*.—Average: 5.3 cm.
*Fruitlets per fruit*.—Average: 52.
*Fruit colour* (*outside*).—Yellow-green; near RHS-CC 152A.
*Flesh color*.—Green; near RHS-CC 143C, darker towards the margins; near RHS-CC 143A.
*Flesh aroma*.—Non-aromatic.
*Fruit core average size and color*.—Average length of core: 5.0 cm, average diameter of core at the base: 9 mm, average diameter of core at the top: 4 mm, core colored yellow-green and greyed-yellow; near RHS-CC 150D and 160C.

What is claimed is:

1. A new and distinct cultivar of *Ananas comosus* plant named 'Duranas2' as herein illustrated and described.

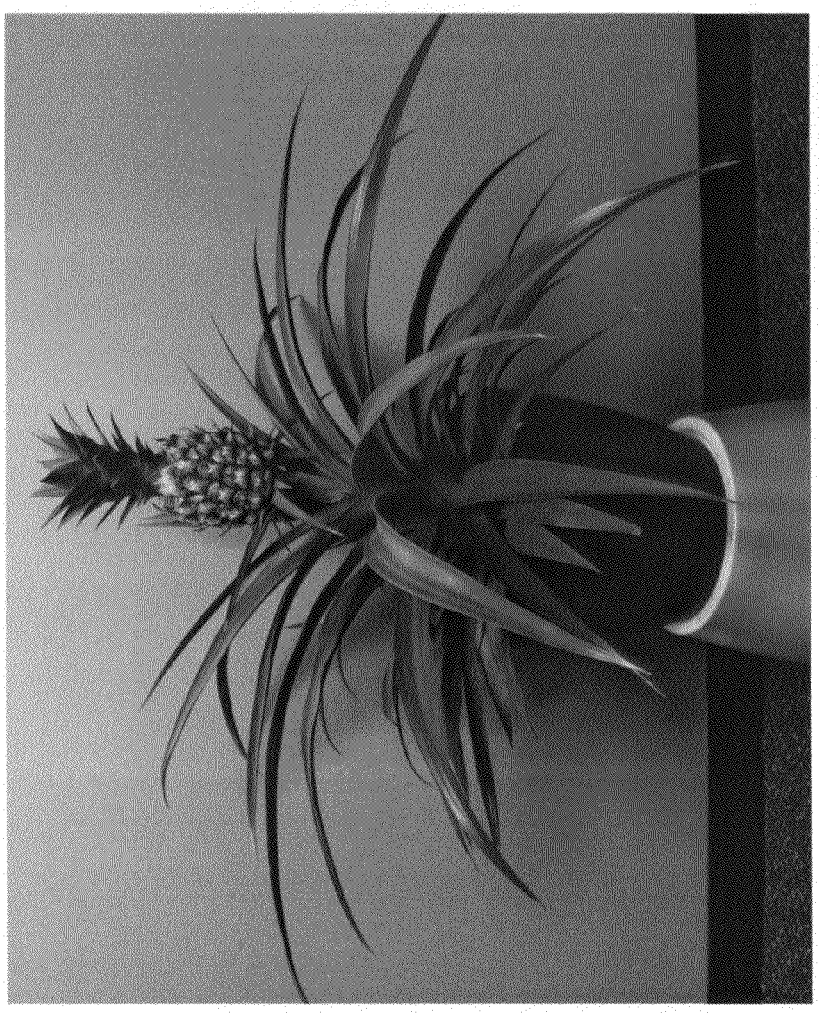

* * * * *